United States Patent [19]

Lew

[11] Patent Number: 5,060,522
[45] Date of Patent: Oct. 29, 1991

[54] MASS-VOLUME VORTEX FLOWMETER

[76] Inventor: Hyok S. Lew, 7890 Oak St., Arvada, Colo. 80005

[21] Appl. No.: 467,486

[22] Filed: Jan. 19, 1990

[51] Int. Cl.$^5$ ........................ G01F 1/32; G01F 15/10
[52] U.S. Cl. ............................. 73/861.02; 73/861.24
[58] Field of Search .......... 73/861.02, 861.03, 861.22, 73/861.24

[56] References Cited

U.S. PATENT DOCUMENTS

| | | | |
|---|---|---|---|
| 4,010,645 | 3/1977 | Herzl | 73/861.03 |
| 4,448,081 | 5/1984 | Kolitsch et al. | 73/861.03 |
| 4,523,477 | 6/1985 | Miller | 73/861.22 |

Primary Examiner—Herbert Goldstein

[57] ABSTRACT

A vortex shedding flowmeter includes at least one total pressure hole emerging through the leading edge of the vortex generator of an elongated cylindrical shape disposed perpendicular to the direction of the fluid flow and at least one static pressure hole emerging through at least one of the two side faces of the vortex generator, wherein the dynamic pressure of the fluid flow is determined from the difference between the total pressure and the static pressure, and the velocity of the fluid is determined from the shedding frequency of vortices shed from the vortex generator; whereby the mass flow rate can be determined from the ratio of the dynamic pressure to the velocity of the fluid and the density of the fluid is determined from the ratio of the mass flow rate to the velocity of the fluid.

21 Claims, 3 Drawing Sheets

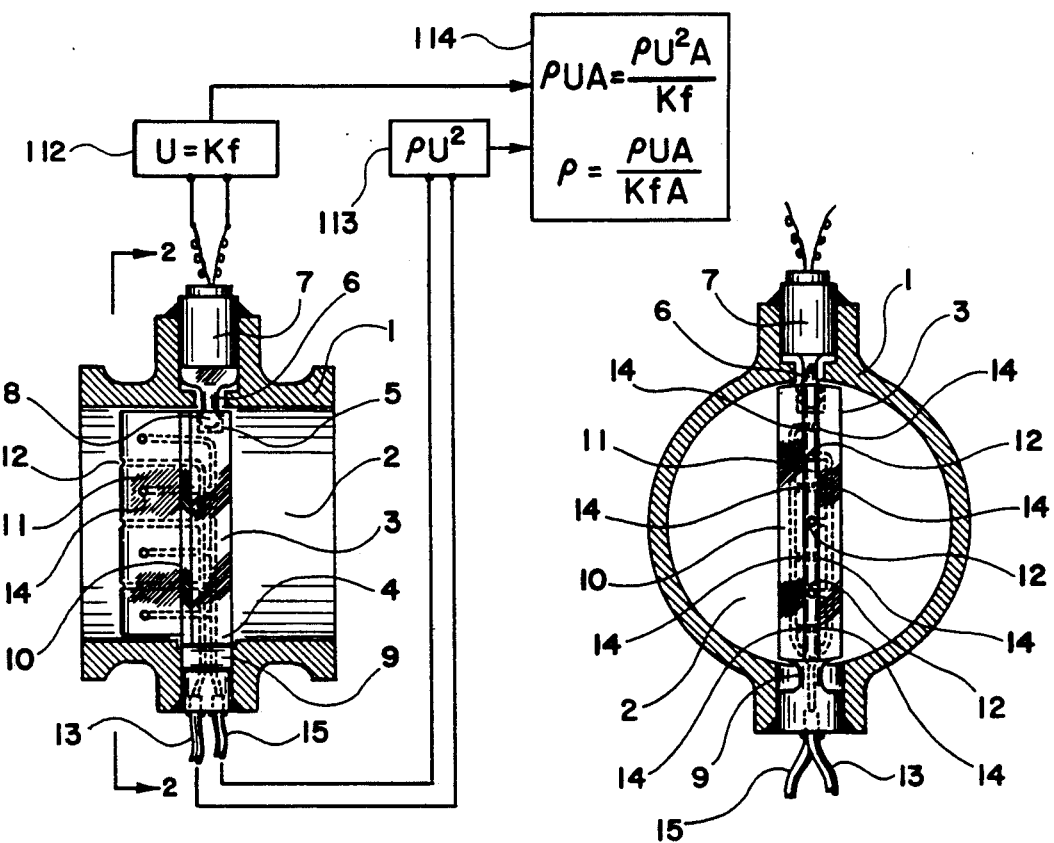
Fig. 1
Fig. 2
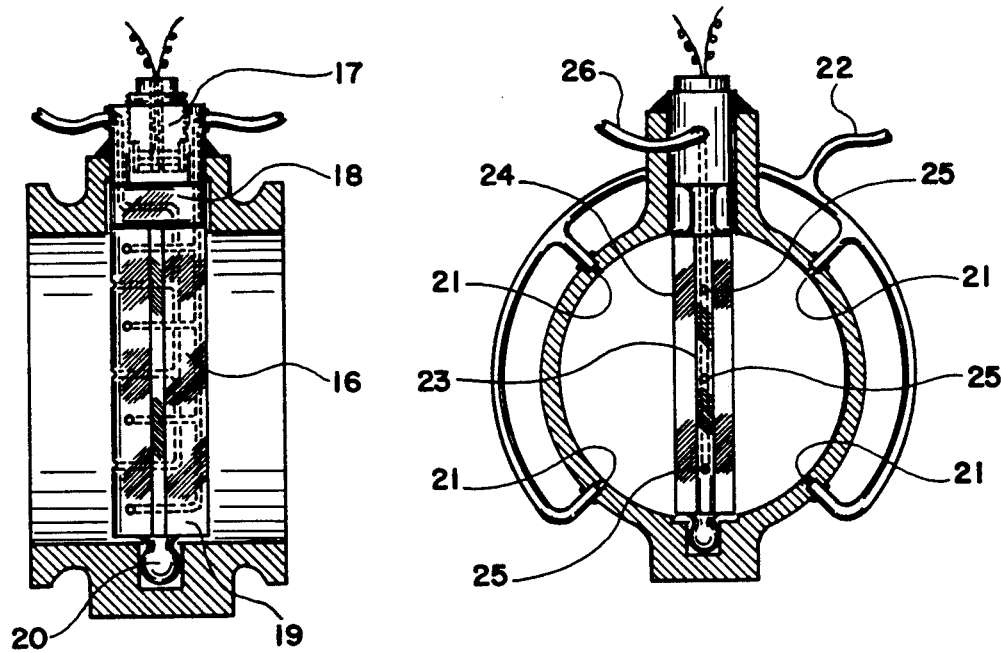
Fig. 3
Fig. 4

MASS-VOLUME VORTEX FLOWMETER

BACKGROUND OF THE INVENTION

The unmistakable trend for the tomorrow's flowmeter technology is the emergence of multiple function flowmeters which measure the mass and volume flow rates as well as the density of the fluid. The Pitot tube has been in use for nearly a hundred years, that determines the dynamic pressure of the fluid flow which is equal to one half of the fluid density times the square of the fluid velocity as the difference between the total pressure and the static pressure of the fluid. The vortex flowmeter, that determines the fluid velocity from the vortex shedding frequency, has become one of the most popular devices in the industrial flow measurements in only fifteen years after its introduction to the industry in mid-seventies. Previously, the inventor of the present invention has invented two different types of the mass-volume flowmeter. One type employs a vortex generating bluff body of a cylindrical shape disposed across a flow passage and a vortex sensor of planar shape disposed downstream of the vortex generating bluff body, wherein the volume flow rate is determined from the frequency of an alternating fluid dynamic force associated with the vortex shedding and experienced by the vortex sensor, and the dynamic pressure of the fluid flow is determined from the amplitude of the alternating fluid dynamic force, which teachings appears in U.S. Pat. No. 4,807,481. Of course, the mass flow rate is obtained from the ratio of the dynamic pressure to the volume flow rate and the density of the fluid is obtained as the ratio of the mass flow rate to the volume flow rate. The other type of the mass-volume flowmeter invented by this inventor employs a pair of parallel flow passages wherein one of the two flow passages includes a variable position flow obstructing body such as a flap or spherical member. The dynamic pressure of the fluid flow on the flow obstructing body opens up the flow passage under obstruction and, consequently, the degree of the obstruction decreases as the dynamic pressure of the fluid flow increases. The volume flow rate is determined as the sum of two signals generated by two volume flow sensors respectively disposed in the two flow passages, while the dynamic pressure of the fluid flow is determined as a function of level of inequality in the flow rate between the two flow passages by using an empirically obtained functional relationship therebetween, which teaching appears in U.S. patent application Ser. No. 07/208,739. The third most logical method for constructing a mass-volume flowmeter is to incorporate the operating principles of the Pitot tube into a vortex shedding flowmeter, which teaching is addressed by the present patent application.

BRIEF SUMMARY OF THE INVENTION

The primary object of the present invention is to provide a vortex generating bluff body of a cylindrical shape disposed at least partially across a flow passage, which vortex generating bluff body includes a planar extension disposed parallel to the direction of the fluid flow and extending from the upstream face of the vortex generating bluff body, wherein the planar extension includes at least one total pressure hole open to the leading edge of the planar extension for tapping the total pressure of the fluid flow.

Another object is to provide a vortex generating bluff body with the planar extension including the total pressure hole that also includes at least one static pressure hole open to at least one of the two side faces of the planar extension parallel to the direction of the fluid flow for tapping the static pressure of the fluid flow.

A further object is to determine the fluid velocity from the frequency of the vortex shedding from the vortex generating bluff body, and to determine the dynamic pressure from the difference between the total pressure and the static pressure of the fluid flow, wherein the mass flow rate is determined from the ratio of the dynamic pressure to the fluid velocity.

Yet another object is to determine the density of the fluid as the ratio of the mass flow rate to the volume flow rate.

Yet a further object is to provide a mass-volume flowmeter comprising a vortex generating bluff body with a planar leading edge extension including the total and static pressure holes, and a vortex sensing planar member disposed downstream of the vortex generating bluff body, which vortex sensing planar member detects the alternating fluid dynamic force generated by the vortices and thereby provides information on the vortex shedding frequency.

Still another object is to provide a mass-volume flowmeter comprising a vortex generating bluff body with a planar leading edge extension including the total and static pressure holes, wherein the vortex generating bluff body is connected to a transducer that converts the fluid dynamic reaction of the vortex shedding to an electrical signal and thereby provides information on the vortex shedding frequency.

Still a further object is to provide a mass-volume flowmeter comprising a vortex generating bluff body with a planar leading edge extension including the total and static pressure holes, and further comprising a vortex sensor and noise sensor built into the vortex shedding bluff body, wherein the signals from the vortex sensor and noise sensor are combined to cancel noises and obtain vortex signal providing information on the vortex shedding frequency.

These and other objects of the present invention will become clear as the description thereof progresses.

BRIEF DESCRIPTION OF THE FIGURES

The present invention may be described with a greater clarity and specificity by referring to the following figures:

FIG. 1 illustrates a cross section of an embodiment of the mass-volume vortex flowmeter comprising a vortex generator-sensor with a plurality of total and static pressure holes.

FIG. 2 illustrates another cross section of the embodiment shown in FIG. 1.

FIG. 3 illustrates a cross section of another embodiment of the mass-volume vortex flowmeter.

FIG. 4 illustrates a cross section of a further embodiment of the mass-volume vortex flowmeter.

DESCRIPTION OF THE ILLUSTRATED EMBODIMENTS

Figure 5:
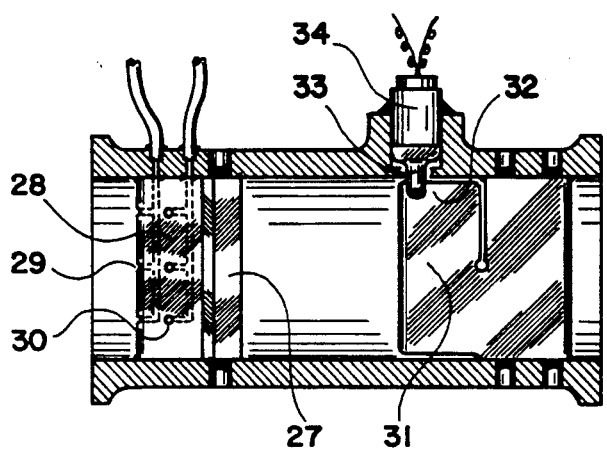
FIG. 5 illustrates a cross section of yet another embodiment of the mass-volume vortex flowmeter.

In FIG. 1 there is illustrated a cross section of an embodiment of the mass-volume vortex flowmeter constructed in accordance with the principles of the present invention. The flowmeter body 1 includes a flow passage 2 extending from one extremity to the other extremity thereof. A vortex generating bluff body 3 of an elongated cylindrical shape is disposed across the flow passage 2, wherein extremity 4 is secured to the flowmeter body 1, while the other extremity 5 is connected to a force transmitting member 6 extending from a transducer container vessel 7 by a mechanical coupling 8 such as a flexible joint, which transducer container vessel may include a pair of Piezo electric element disposed on the two opposite sides of a plane including the central axis of the force transmitting member 6 and parallel to the direction of the fluid flow. The extremity 4 of the vortex generating bluff body 3 has a thin section 9 that enhances the flexural deflection thereof under an alternating lateral fluid dynamic force generated by vortices shed from the two opposite sides of the vortex generating bluff body 3 in an alternating pattern. The blunt upstream face 10 of the vortex generating bluff body 3 includes a planar leading edge extension 11 disposed parallel to the direction of the fluid flow and extending from the blunt upstream face 10 of the bluff body 3. A plurality of total pressure holes 12 is open to the leading edge of the planar leading edge extension 11, which are connected to the total pressure conduit 13, while a plurality of static pressure holes 14 are open to the two sides of the planar leading edge extension 11, which are connected to the static pressure conduit 15.

In FIG. 2 there is illustrated another cross section of the embodiment shown in FIG. 1, which cross section clearly illustrates the distribution of the total and static pressure holes 12 and 14, as well as the thin section 9 adjacent to the anchored end of the vortex generating bluff body 3.

In FIG. 3 there is illustrated a cross section of another embodiment of the mass-volume vortex flowmeter that has a vortex generating bluff body 16 with the total and static pressure holes, which has essentially the same construction as the corresponding element included in the embodiment shown in FIGS. 1 and 2 with a few exceptions. In this embodiment, the vortex generating bluff body 16 with the total and static pressure holes and the transducer container vessel 17 are constructed in an integrated structure, wherein a thin section 18 is included therebetween, while the extremity 19 of the vortex generating bluff body 16 is simply supported by the flowmeter body by means of the ball and socket joint 20. The combination of the thin section 18 and the simple support 20 enhances the transmission of the alternating fluid dynamic force generated by the vortex shedding and experienced by the vortex generating bluff body 16 to the Piezo electric transducer contained in the transducer container vessel 17. It should be mentioned that the combination of the transducer vessel 17 and the vortex generating bluff body 16 may be fastened to the flowmeter body by means of a flange coaxially affixed to the transducer container vessel 17 and fastened to the flowmeter body by screws in place of the weld connection employed in the particular illustrated embodiment.

In FIG. 4 there is illustrated a cross section of a further embodiment of the mass-volume vortex flowmeter that has essentially the same construction as that of the embodiment shown in FIG. 3 with one exception, which exception is the static pressure holes 21 now emerging through the wall of the flow passage, which static pressure holes are connected to the static pressure conduit 22, while the planar leading edge extension 23 of the vortex generating bluff body 24 now includes the plurality of the total pressure holes 25 only, which are connected to the total pressure conduit 26. The embodiment shown in FIGS. 1 and 2 may also be modified to an arrangement similar to that shown in FIG. 4, wherein the static pressure holes are included in the wall of the flow passage instead of the planar leading edge extension of the vortex generating bluff body.

In FIG. 5 there is illustrated a cross section of yet another embodiment of the mass-volume vortex flowmeter, that comprises a vortex generating bluff body 27 with a planar leading edge extension 28 including the total and static pressure holes 29 and 30, which vortex generating bluff body is disposed across a flow passage and secured to the wall of the flow passage. A vortex sensor 31 of a planar geometry is disposed downstream of the vortex generating bluff body across the flow passage on a plane generally parallel to the central axis of the flow passage, wherein at least an extremity of the vortex sensor 31 is secured to the wall of the flow passage, while a deflective portion 32 thereof is connected to a force transmitting member 33 extending from a transducer container vessel 34.

The mass-volume vortex flowmeters shown in FIGS. 1-5 operate on the following principles: The velocity of the fluid moving through the flow passage is determined from the vortex shedding frequency obtained from the information provided by the transducer converting the alternating fluid dynamic force generated by the vortices to an alternating electrical signal, as the fluid velocity is linearly proportional to the vortex shedding frequency in a wide range of the fluid velocity. The dynamic pressure, that is equal to one half of the fluid density times the square of the fluid velocity, is determined as the difference between the total pressure and static pressure, which pressure difference is measured by a differential pressure transducer or manometer connected to the total and static pressure conduits included in the mass-volume vortex flowmeter. The mass flow rate is determined as the ratio of the dynamic pressure to one half of the fluid velocity. The density of the fluid is obtained as the ratio of the mass flow rate to the fluid velocity.

The above-described algorithms determining the mass flow rate and the density of the fluid from the measured value of the fluid velocity and the measured values of the total and static pressures are carried out by the data processors shown in FIG. 1. The first data processor 112 determines the fluid velocity U by multiplying an empirically determined constant of proportionality K to the measured value of the vortex shedding frequency. A second data processor 113 determines the dynamic pressure $\rho U^2$ from a differential combination of the measured values of the total pressure and static pressure. A third data processor 114 determines the mass flow rate $\rho UA$ and the fluid density $\rho$ by using the fluid velocity U supplied by the first data processor 112, the dynamic pressure $\rho U^2$ supplied by the second data processor 113 and the cross sectional area A of the flow passage stored therein.

Figure 6:
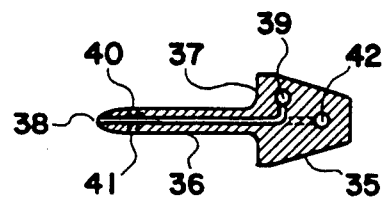
FIG. 6 illustrates a cross section of an embodiment of the vortex generating bluff body with the total and static pressure holes.

In FIG. 6 there is illustrated a cross section of an embodiment of the vortex generating bluff body 35 with a planar leading edge extension 36 extending from the blunt upstream face 37 of the vortex generating bluff body 35. A single or plurality of the total pressure holes 38 open to the leading edge of the planar leading edge extension 36 are disposed following the length of the planar leading edge extension, which total pressure holes 38 are connected to the total pressure conduit 39 included in the bluff body in the lengthwise direction thereof, and extending through and out of the flow passage wall. A single or plurality of the pair of the static pressure holes 40 and 41 are open to the two side faces of the planar leading edge extension 36 and connected to the static pressure conduit 42 disposed lengthwise through the bluff body 35 and extending through the flow passage wall.

Figure 7:
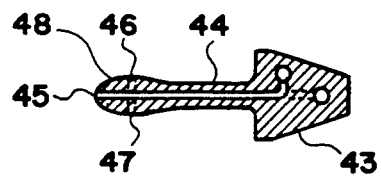
FIG. 7 illustrates a cross section of another embodiment of the vortex generating bluff body with the total and static pressure holes.

In FIG. 7 there is illustrated a cross section of another embodiment of the vortex generating bluff body with a planar leading edge extension 44 including the total pressure holes 45 and the static pressure holes 46 and 47, which has essentially the same construction as the embodiment shown in FIG. 6 with one exception. The leading edge portion of the cross section of the planar leading edge extension 44 includes a thick section 48 providing a bulbous leading edge. This particular embodiment is useful in constructing a vortex generating bluff body with a small width, wherein the planar leading edge extension must have a very small thickness.

Figure 8:
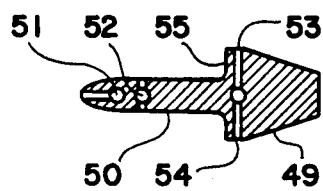
FIG. 8 illustrates a cross section of a further embodiment of the vortex generating bluff body with the total and static pressure holes.

In FIG. 8 there is illustrated a cross section of a further embodiment of the vortex generating bluff body 49 with a planar leading edge extension 50, that has essentially the same construction as the embodiment shown in FIGS. 6 with a few exception being the placement of the total pressure conduit 51 and the static pressure conduit 52, which are now disposed lengthwise in the planar leading edge extension 50 instead of the bluff body 49. In an alternative design, the static pressure holes open to the two sides of the leading edge extension 50 may be replaced with the static pressure holes 53 and 54 open to the two side faces of the bluff body 49 at a location adjacent to the blunt upstream face 55 of the bluff body 49. Such an alternative design provides an enhanced sensitivity to the mass-volume vortex flowmeter at the expense of a reduced accuracy, as the dynamic pressure is merely proportional to the difference between the total pressure and the static pressure wherein the constant of proportionality may vary slightly as a function of the fluid velocity.

Figure 9:
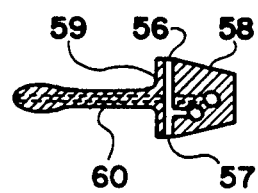
FIG. 9 illustrates a cross section of yet another embodiment of the vortex generating bluff body with the total and static pressure holes.

In FIG. 9 there is illustrated a cross section of yet another embodiment of the vortex generating bluff body that has essentially the same construction as that of the embodiment shown in FIG. 7 with one exception, which is the location of the static pressure holes 56 and 57 now open to the two opposite side faces of the bluff body 58 at a location adjacent to the blunt upstream face 59 thereof instead of the two sides of the planar leading edge extension 60.

Figure 10:
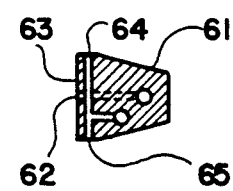
FIG. 10 illustrates a cross section of yet a further embodiment of the vortex generating bluff body with the total and static pressure holes.

In FIG. 10 there is illustrated a cross section of yet a further embodiment of the vortex generating bluff body 61 without the planar leading edge extension. The total pressure holes 62 are disposed following the center line of the blunt upstream face 63 of the bluff body 61, while the static pressure holes 64 and 65 are open to the two side faces of the bluff body at a location adjacent to the blunt upstream face 63 of the bluff body 61. The embodiments of the vortex generating bluff body shown in FIGS. 6, 7, 8, 9 and 10 are suitable for the construction of the mass-volume vortex flowmeters shown in FIGS. 1, 3, 4 and 5. It should be understood that, when the arrangement of the total pressure conduit and that of the static pressure conduit do not extend from the planar leading edge extension to the bluff body as exemplified by the embodiments shown in FIG. 8, the planar leading edge extension may not be physically attached to the blunt upstream face of the bluff body as shown in FIG. 13.

Figure 11:
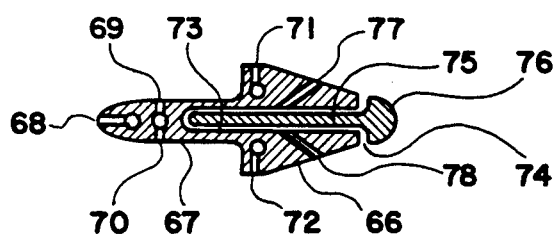
FIG. 11 illustrates a cross section of still another embodiment of the vortex generating bluff body with the total and static pressure holes.

In FIG. 11 there is illustrated a cross section of still another embodiment of the vortex generating bluff body 66 with the planar leading edge extension 67 including the total pressure holes 68, wherein the static pressure holes may be included in the planar leading edge extension 67 as exemplified by the holes 69 and 70, or in the bluff body 66 as exemplified by the holes 71 and 72. The combination of the bluff body 66 and the planar leading edge extension 67 has a deep planar groove 73 disposed parallel to the center plane of the combination and extending thereinto from the downstream face 74 of the bluff body 66, which planar groove 73 receives a pressure panel 75 with a rigid trailing edge 76 in a spaced relationship therebetween. The two side walls of the planar groove 73 may include a plurality of holes or openings 77 and 78 respectively extending therethrough and emerging through the two side faces of the bluff body 66. The combination of the bluff body 66 and the planar leading edge extension 67 must be secured rigidly to the flowmeter body at least one extremity thereof, while one extremity of the pressure panel 75 is connected or coupled to the force transmitting member, such as the element 6 shown in FIG. 1 or element 18 in shown in FIG. 3, extending from the transducer container vessel. The embodiment of the vortex generating bluff body shown in FIG. 11 is particularly suitable for the construction of an insertion type mass-volume vortex flowmeter shown in FIG. 15.

Figure 12:
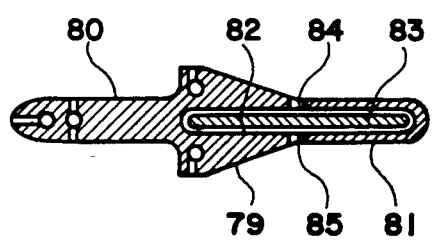
FIG. 12 illustrates a cross section of still a further embodiment of the vortex generating bluff body with the total and static pressure holes.

In FIG. 12 there is illustrated a cross section of still a further embodiment of the vortex generating bluff body 79 with a planar leading edge extension 80 and a planar trailing edge extension 81, wherein the total pressure holes are included in the planar leading edge extension 80, while the static pressure holes may be included either in the planar leading edge extension 80 or in the bluff body 79. The combination of the bluff body 79 and the planar leading and trailing edge extensions 80 and 81 includes a planar cavity 82 disposed parallel to the center plane of the combination, which planar cavity 82 houses a pressure panel 83 in a spaced relationship therebetween. The two side walls of the planar cavity 82 include a plurality of holes 84 and 85 respectively emerging through the two side faces of the bluff body 79. The combination of the bluff body 79 and the planar leading and trailing edge extensions 80 and 81 must be rigidly secured to the flowmeter body at at least one extremity thereof, while one extremity of the pressure panel 83 is connected or coupled to the force transmitting member extending from the transducer container vessel as described in conjunction with FIG. 11. In an alternative design, the planar trailing edge extension 81 can be omitted, wherein the planar cavity 82 is included in the combination of the bluff body 79 and the planar leading edge extension 80. In such an alternative design, the pressure communicating holes 84 and 85 should be located intermediate the blunt upstream face and the downstream face of the bluff body as shown in FIG. 11. The embodiment of the vortex generating bluff body shown in FIG. 12 is particularly suitable for the construction of an insertion type mass-volume vortex flowmeter shown in FIG. 16.

Figure 13:
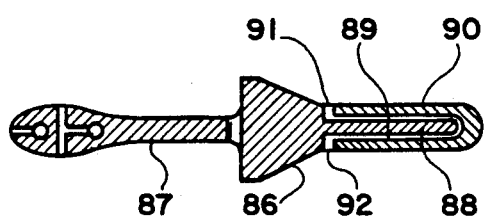
FIG. 13 illustrates a cross section of yet still another embodiment of the vortex generating bluff body with the total and static pressure holes.
Figure 17:
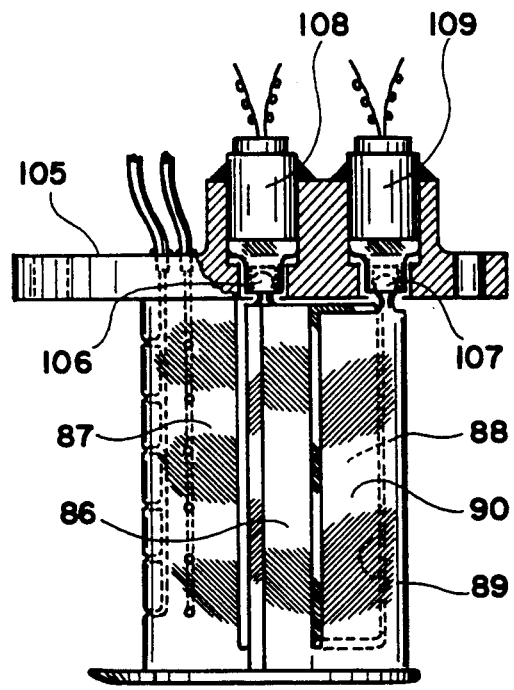
FIG. 17 illustrates a construction of the vortex generating bluff body with the total and static pressure holes, that has the cross section shown in FIG. 13.

In FIG. 13 there is illustrated a cross section of yet still another embodiment of the vortex generating bluff body 86 including the planar leading edge extension 87 disposed upstream thereof and a planar trailing edge extension 88 engaging a deep planar groove 89 included in a planar member 90 disposed downstream of the bluff body 86. The gaps 91 and 92 between the bluff body 86 and the planar member 90 provide the pressure communications between the two side faces of the bluff body 86 and the two sides of the planar trailing edge extension 88, respectively. The planar leading edge extension 89 including the total and static pressure holes may be physically separated from the bluff body as shown in the particular illustrated embodiment or may be physically attached to the bluff body as exemplified by the embodiments shown in FIGS. 11 or 12. One extremity of the combination of the bluff body 86 and the planar trailing edge extension 88 must be connected or coupled to the force transmitting member extending from the transducer container vessel, while the planar leading edge extension 87 and the planar member 90 are rigidly secured to the flowmeter body at one or both extremities thereof. In an alternative design, one extremity of the planar member 90 may be connected or coupled to a force transmitting member extending from a second transducer container vessel as shown in FIG. 17, whereby the signals from the two transducers are combined to cancel the noises generated by mechanical vibrations and obtain a refined signal representing the vortex shedding.

Figure 14:
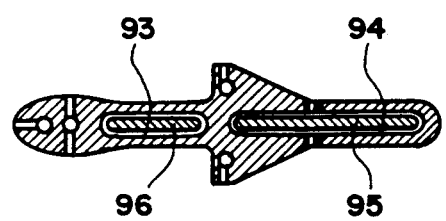
FIG. 14 illustrates a cross section of yet still a further embodiment of the vortex generating bluff body with the total and static pressure holes.
Figure 18:
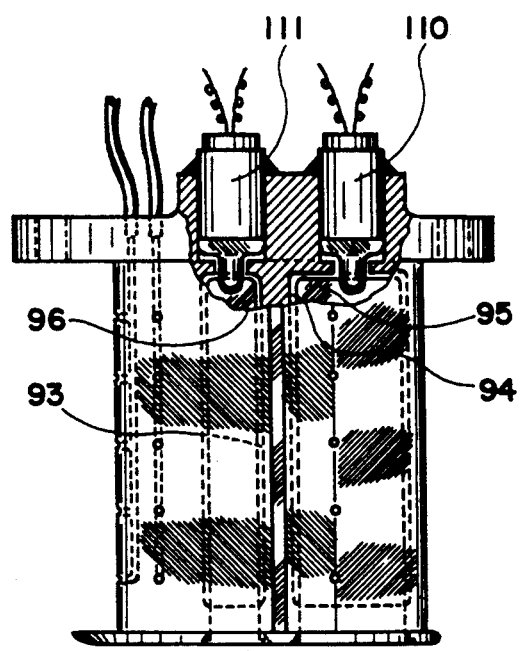
FIG. 18 illustrates a construction of the vortex generating bluff body with the total and static pressure holes, that has the cross section shown in FIG. 14.

In FIG. 14 there is illustrated a cross section of yet still a further embodiment of the vortex generating bluff body, that has essentially the same construction as the embodiment shown in FIG. 12 with one exception, which is the second cavity 93 included in the combination of the bluff body and the planar leading and trailing edge extensions, that is disposed parallel to the first cavity 94 housing the pressure panel 95 responding to the alternating pressure fluctuations created by the vortex shedding. The second cavity 93 sealed off from the fluid houses an elongated member 96 connected or coupled to a force transmitting member extending from a second transducer container vessel as shown in FIG. 18, whereby the signals from the two transducers are combined to cancel noises generated by mechanical vibrations and obtain a refined signal representing the vortex shedding.

Figure 15:
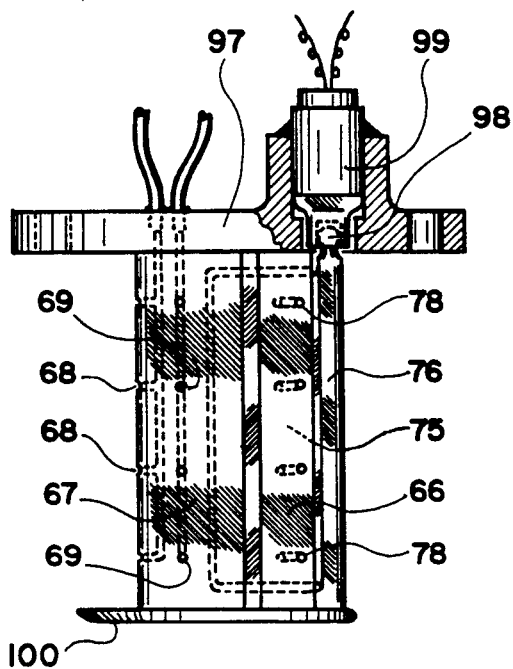
FIG. 15 illustrates a construction of the vortex generating bluff body with the total and static pressure holes, that has the cross section shown in FIG. 11.

In FIG. 15 there is illustrated an embodiment of the mass-volume vortex flowmeter employing the vortex generating bluff body having the cross section shown in FIG. 11. The combination of the bluff body 66 and the planar leading edge extension 67 is rigidly secured to the flowmeter body or the anchoring flange 97 at one or both extremities thereof. One extremity of the reinforced trailing edge 76 of the pressure panel 75 is connected or coupled to the force transmitting member 98 extending from a transducer container vessel 99, while the other extremity is secured to the bluff body 66 as exemplified by the particular illustrative embodiment or to the flowmeter body in an alternative design. When one extremity of the combination of the bluff body 66 and the planar leading edge extension 67 is terminated in the middle of the fluid stream as in the case of the insertion type mass-volume vortex flowmeter exemplified by the particular illustrative embodiment, that extremity should include a planar flow guide 100 which maintains the rectilinear planar flow following planes perpendicular to the lengthwise axis of the bluff body.

Figure 16:
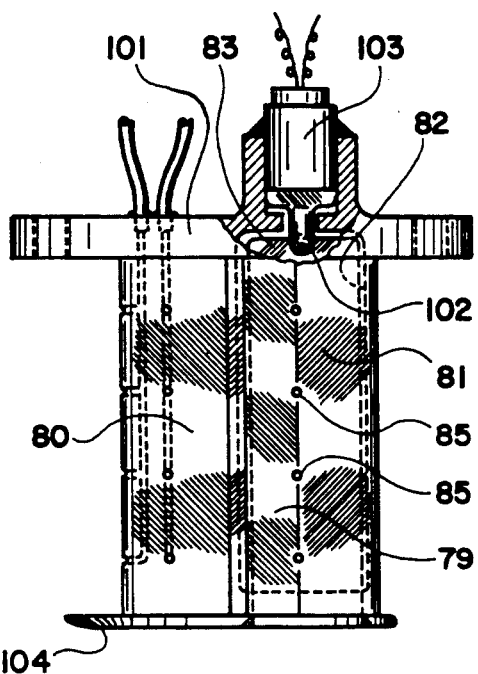
FIG. 16 illustrates a construction of the vortex generating bluff body with the total and static pressure holes, that has the cross section shown in FIG. 12.

In FIG. 16 there is illustrated an embodiment of the mass-volume vortex flowmeter employing the vortex generating bluff body having the cross section shown in FIG. 12. The combination of the bluff body 79 and the planar leading and trailing edge extensions 80 and 81 is secured to the flowmeter body or anchoring flange 101 at one or both extremities thereof. One extremity of the pressure panel 83 housed in the planar cavity 82 is connected or coupled to a force transmitting member 102 extending from a transducer container vessel 103, while the other extremity is secured to the bluff body 79 as shown in the particular illustrative embodiment or to the flowmeter body in an alternative embodiment. The planar flow guide 104 should be included in the construction of an insertion type mass-volume vortex flowmeter, as it enhances the vortex shedding from the bluff body 79 in a clear and regular pattern.

In FIG. 17 there is illustrated an embodiment of the mass-volume vortex flowmeter employing the vortex generating bluff body having the cross section shown in FIG. 13. In the particular illustrative embodiment of an insertion type mass-volume vortex flowmeter, the planar leading edge extension 87 is rigidly secured to the anchoring flange !05 at one extremity thereof. The bluff body 86 separated from the planar leading edge extension 87 over entire length thereof except the extremity opposite to the secured extremity of the planar leading edge extension 87 is supported by the planar leading edge extension 87 at the over-hanging extremities thereof. The planar member 90 with a deep groove 89 shielding the trailing edge planar extension 88 of the bluff body 86 is also supported by the planar leading edge extension 87 at the overhanging extremity thereof.

The unsupported extremities of the bluff body 86 and the planar member 90 are respectively connected or coupled to two force transmitting members 106 and 107 respectively extending from two transducer container vessels 108 and 109. The signals from the two transducers 108 and 109 are combined to cancel the mechanical vibration noises and obtain a noise-free signal representing the vortex shedding, from which the vortex shedding frequency is determined. If the mechanical vibration noises are not problematic in determining the vortex shedding frequency, the second transducer 109 may be omitted and both extremities of the planar member 90 can be secured to the flowmeter body or the anchoring flange. In general, the mechanical vibration noises pose a serious problem in the insertion type vortex flowmeter and, consequently, the noise cancelling features employing the dual transducer system is required.

In FIG. 18 there is illustrated an embodiment of the mass-volume flowmeter employing the vortex generating bluff body having the cross section shown in FIG. 14, which has essentially the same construction as the embodiment shown in FIG. 16 with one exception, which is the inclusion of the elongated member 96 housed in the sealed planar cavity 93, that is disposed parallel to the pressure panel 95 housed in the planar cavity 94 including pressure communication holes open to the two side faces of the bluff body. The two transducer container vessels 110 and 111 respectively connected or coupled to the planar members 95 and 96 generate two electrical signals, which can be combined to cancel the mechanical vibration noises and obtain a refined signal representing the vortex shedding, from which the vortex shedding frequencies is determined. The fluid velocity is determined from the vortex shedding frequency based on a linear relationship therebetween obtained empirically. The dynamic pressure of the fluid flow is obtained as the difference between the total pressure and the static pressure. The volume and mass flow rates as well as the density of the fluid are determined from combinations of the fluid velocity and the dynamic pressure of the fluid flow. In the particular illustrative embodiment shown in FIG. 18, those extremities of the two planar members 95 and 96 opposite to the extremities connected or coupled to the transducer container vessels 110 and 111 are anchored to the over-hanging extremity of the combination of the bluff body and the planar leading and trailing edge extensions. In an alternative embodiment, the planar members 95 and 96 may be respectively affixed to the two transducer container vessels 110 and 111, and extending therefrom in a cantilever arrangement.

While the principles of the present inventions have now been made clear by the illustrative embodiments, there will be many modifications of the structures, arrangements, proportions, elements and materials obvious to those skilled in the art, which are particularly adapted to the specific working environments and operating conditions in the practice of the inventions without departing from those principles. It is not desired to limit the inventions to the particular illustrative embodiments shown and described and, accordingly, all suitable modifications and equivalents may be regarded as falling within the scope of the inventions as defined by the claims which follow.

The embodiments of the invention, in which an exclusive property or privilege is claimed, are defined as follows:

1. An apparatus for measuring flow rate of fluid comprising in combination:
    a) a vortex generator of an elongated cylindrical shape disposed generally perpendicular to the direction of fluid flow, said vortex generator having a blunt upstream face and a planar member disposed generally parallel to the direction of fluid flow on a plane generally including the central axis of the vortex generator immediately adjacent to said blunt upstream face of the vortex generator;
    b) at least one hole emerging through leading edge of said planar member and connected to a first conduit for tapping total pressure of the fluid flow;
    c) at least one hole emerging through at least one of the two side surface of said planar member and connected to a second conduit for tapping static pressure of the fluid flow;
    d) means for measuring shedding frequency of vortices shed from the vortex generator; and
    e) means for determining dynamic pressure of the fluid flow from a differential combination of the total pressure and the static pressure of the fluid flow.

2. The combination as set forth in claim 1 wherein said combination includes means for determining velocity of the fluid from the shedding frequency of vortices, and mass flow rate of the fluid from the ratio of the dynamic pressure of the fluid flow to the velocity of the fluid.

3. The combination as set forth in claim 2 wherein said combination includes means for determining density of the fluid from the ratio of the mass flow rate to the velocity of the fluid.

4. The combination as set forth in claim 1 wherein the leading edge of said planar member includes a rounded thick section in the cross section thereof.

5. The combination as set forth in claim 1 wherein said planar member extends from said blunt upstream face of the vortex generator.

6. The combination as set forth in claim 1 wherein said means for measuring the shedding frequency of vortices comprises a transducer connected to the vortex generator, that converts a fluctuating fluid dynamic force associated with vortices shed from the vortex generator to a fluctuating electrical signal.

7. The combination as set forth in claim 1 wherein said means for measuring the shedding frequency of vortices comprises a downstream planar member disposed downstream of the vortex generator and a transducer connected to the downstream planar member that converts a fluctuating fluid dynamic force associated with vortices shed from the vortex generator and experienced by the downstream planar member to a fluctuating electrical signal.

8. The combination as set forth in claim 1 wherein said means for measuring the shedding frequency of vortices comprises a pressure panel disposed in a narrow groove included in the vortex generator generally parallel to the direction of fluid flow and open to the downstream face of the vortex generator, ad a transducer connected to said pressure panel, wherein said transducer converts a fluctuating pressure force associated with vortices shed from the vortex generator and experienced by said pressure panel to a fluctuating electrical signal.

9. The combination as set forth in claim 8 wherein said combination includes at least one opening extending from the narrow groove to one of the two opposite side faces of the vortex generator.

10. The combination as set forth in claim 1, wherein said means for measuring the shedding frequency of vortices comprises a pressure panel disposed in a planar cavity included in the vortex generator generally parallel to the direction of the fluid flow wherein two side walls of the planar cavity respectively include at least one opening emerging through one of the two side faces of the vortex generator, and a transducer connected to said pressure panel, that converts a fluctuating pressure force associated with vortices shed from the vortex generator and experienced by said pressure panel to a fluctuating electrical signal.

11. The combination as set forth in claim 10 wherein said combination includes an elongated member disposed generally parallel to said pressure panel in a sealed elongated cavity included in the vortex generator and connected to another transducer that converts mechanical vibrations experienced by said elongated member to a fluctuating electrical signal, whereby the fluctuating electrical signals generated by said a transducer and said another transducer are combined to cancel noises generated by mechanical vibrations and obtain a refined signal representing vortex shedding from the vortex generator.

12. The combination as set forth in claim 11 wherein said planar cavity is open to downstream face of the vortex generator.

13. The combination as set forth in claim 1 wherein the vortex generator includes another planar member disposed generally parallel to the direction of fluid flow on a plane generally including the central axis of the vortex generator and extending from downstream face of the vortex generator, wherein said another planar member engages a narrow groove included in a downstream planar member disposed generally parallel to the direction of fluid flow and adjacent to the downstream face of the vortex generator.

14. The combination as set forth in claim 13 wherein said means for measuring shedding frequency of vortices comprises a transducer connected to the vortex generator, that converts a fluctuating fluid dynamic force associated with vortices shed from the vortex generator to a fluctuating electrical signal.

15. The combination as set forth in claim 14 wherein said combination includes another transducer connected to said downstream planar member, that converts vibrations experienced by said downstream planar member to a fluctuating electrical signal whereby the fluctuating electrical signals generated by said a transducer and said another transducer are combined to cancel noises generated by mechanical vibrations and obtain a refined signal representing vortex shedding from the vortex generator.

16. An apparatus for measuring flow rate of fluid comprising in combination:
a) a vortex generator of an elongated cylindrical shape disposed generally perpendicular to the direction of fluid flow, said vortex generator having a blunt upstream face and a planar member disposed generally parallel to the direction of fluid flow on a plane generally including the central axis of the vortex generator immediately adjacent to said blunt upstream face of the vortex generator;
b) at least one hole emerging through leading edge of said planar member and connected to a first conduit for tapping total pressure of the fluid flow;
c) at least one hole emerging through at least one side surface of the vortex generator downstream of the blunt upstream face of the vortex generator and connected to a second conduit for tapping static pressure of the fluid flow;
d) means for measuring shedding frequency of vortices shed from the vortex generator; and
e) means for determining dynamic pressure of the fluid flow from a differential combination of the total pressure and the static pressure of the fluid flow.

17. The combination as set forth in claim 16 wherein said combination includes means for determining velocity of the fluid from the shedding frequency of vortices, and mass flow rate of the fluid from the ratio of the dynamic pressure of the fluid flow to the velocity of the fluid.

18. The combination as set forth in claim 17 wherein said combination includes means for determining density of the fluid from the ratio of the mass flow rate to the velocity of the fluid.

19. An apparatus for measuring flow rate of fluid comprising in combination:
a) a vortex generator of an elongated cylindrical shape disposed across a cross section of a flow passage generally perpendicular to the direction of fluid flow, said vortex generator having a blunt upstream face and a planar member disposed generally parallel to the direction of fluid flow on a plane generally including the central axis of the vortex generator immediately adjacent to said blunt upstream face of the vortex generator;
b) at least one hole emerging through leading edge of said planar member and connected to a first conduit for tapping total pressure of the fluid flow;
c) at least one hole emerging through a wall of the flow passage disposed generally parallel to the direction of fluid flow and connected to a second conduit for tapping static pressure of the fluid flow;
d) means for measuring shedding frequency of vortices shed from the vortex generator; and
e) means for determining dynamic pressure of the fluid flow from a differential combination of the total pressure and the static pressure of the fluid flow.

20. The combination as set forth in claim 19 wherein said combination includes means for determining velocity of the fluid from the shedding frequency of vortices, and mass flow rate of the fluid from the ratio of the dynamic pressure of the fluid flow to the velocity of the fluid.

21. The combination as set forth in claim 20 wherein said combination includes means for determining density of the fluid from the ratio of the mass flow rate to the velocity of the fluid.

* * * * *